US00PP32512P2

(12) United States Plant Patent
Wood

(10) Patent No.: US PP32,512 P2
(45) Date of Patent: Nov. 24, 2020

(54) ***HYDRANGEA* PLANT NAMED 'SMNHPK'**

(50) Latin Name: *Hydrangea paniculata*
Varietal Denomination: SMNHPK

(71) Applicant: Spring Meadow Nursery, Inc., Grand Haven, MI (US)

(72) Inventor: Timothy D Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/602,616

(22) Filed: Nov. 7, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct cultivar of *Hydrangea* plant named 'SMNHPK' is disclosed, characterized by a unique dwarf size, and attractive, well-shaped habit. Panicles changing color with maturity, creating long term ornamental interest. The new variety is a *Hydrangea*, normally produced as an ornamental plant.

3 Drawing Sheets

Latin name of the genus and species: *Hydrangea paniculata.*

Variety denomination: 'SMNHPK'.

BACKGROUND OF THE INVENTION

The new *Hydrangea* cultivar is a product of a planned breeding program conducted by the inventor, at a commercial nursery in Grand Haven, Mich. The objective of the breeding program was to produce new *Hydrangea* varieties with new habits and strong stems. The open pollination resulting in this new variety was made during Summer of 2011.

The seed parent is the unpatented variety *Hydrangea paniculata* 'Bicolor Pink'. The pollen parent is unknown, as this was the result of open pollination. The new variety was identified as a potentially interesting selection in the Summer of 2015, at a commercial greenhouse in Grand Haven, Mich. Date of first sale was Jun. 25, 2019, occurring in the United States. This sale was made directly by the inventor or one who obtained the claimed invention directly or indirectly from the inventor. This sale and all public disclosures made between Jun. 25, 2019 and the filing of this application fall within the exception allowed under 102(b)(1).

Asexual reproduction of the new cultivar 'SMNHPK' by vegetative softwood cuttings was first performed during 2015, at a commercial greenhouse in Grand Haven, Mich. Subsequent asexual propagation has shown that the unique features of this cultivar are stable and reproduced true to type in 5 successive generations.

SUMMARY OF THE INVENTION

The cultivar 'SMNHPK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHPK' These characteristics in combination distinguish 'SMNHPK' as a new and distinct *Hydrangea* cultivar:

1. Panicles changing color with maturity, creating long term ornamental interest.
2. Dwarf plant.
3. Attractive, well-shaped habit.
4. Hardy in USDA Zones 3-9.

PARENT COMPARISON

Plants of the new cultivar 'SMNHPK' are similar to plants of the seed parent in most horticultural characteristics, however, plants of the new cultivar 'SMNHPK' differ in the following;

1. The new variety has white flowers, turning pink, while the seed parent has green flowers.
2. The new variety is a smaller, more dwarf plant than the seed parent.

COMMERCIAL COMPARISON

Plants of the new cultivar 'SMNHPK' can be compared to the variety *Hydrangea paniculata* 'SMHPFL', U.S. Plant Pat. No. 25,135. These varieties are similar in most horticultural characteristics; however, 'SMNHPK' differs in the following:

1. The new variety is more dwarf than this comparator.
2. Flowers of the new variety fade to a lighter pink color in the late Summer than this comparator.

BRIEF DESCRIPTION OF THE PHOTOGRAPHS

'SMNHPK' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years.

DETAILED BOTANICAL DESCRIPTION

Figure 1:
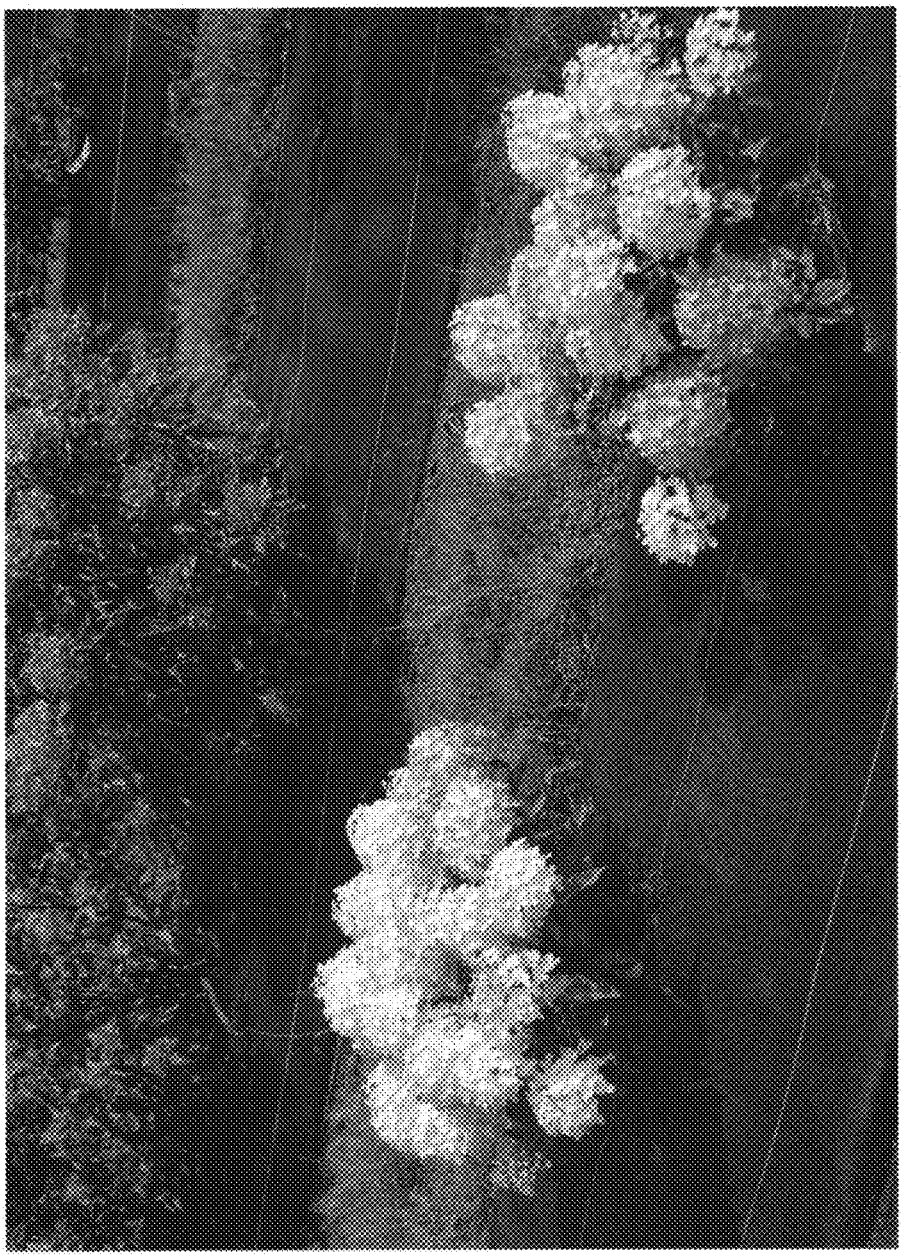
FIG. 1 shows plants of 'SMNHMP' grown outdoors in Grand Haven, Mich. during mid-Summer. Plants have both white and pink flowers.
Figure 2:
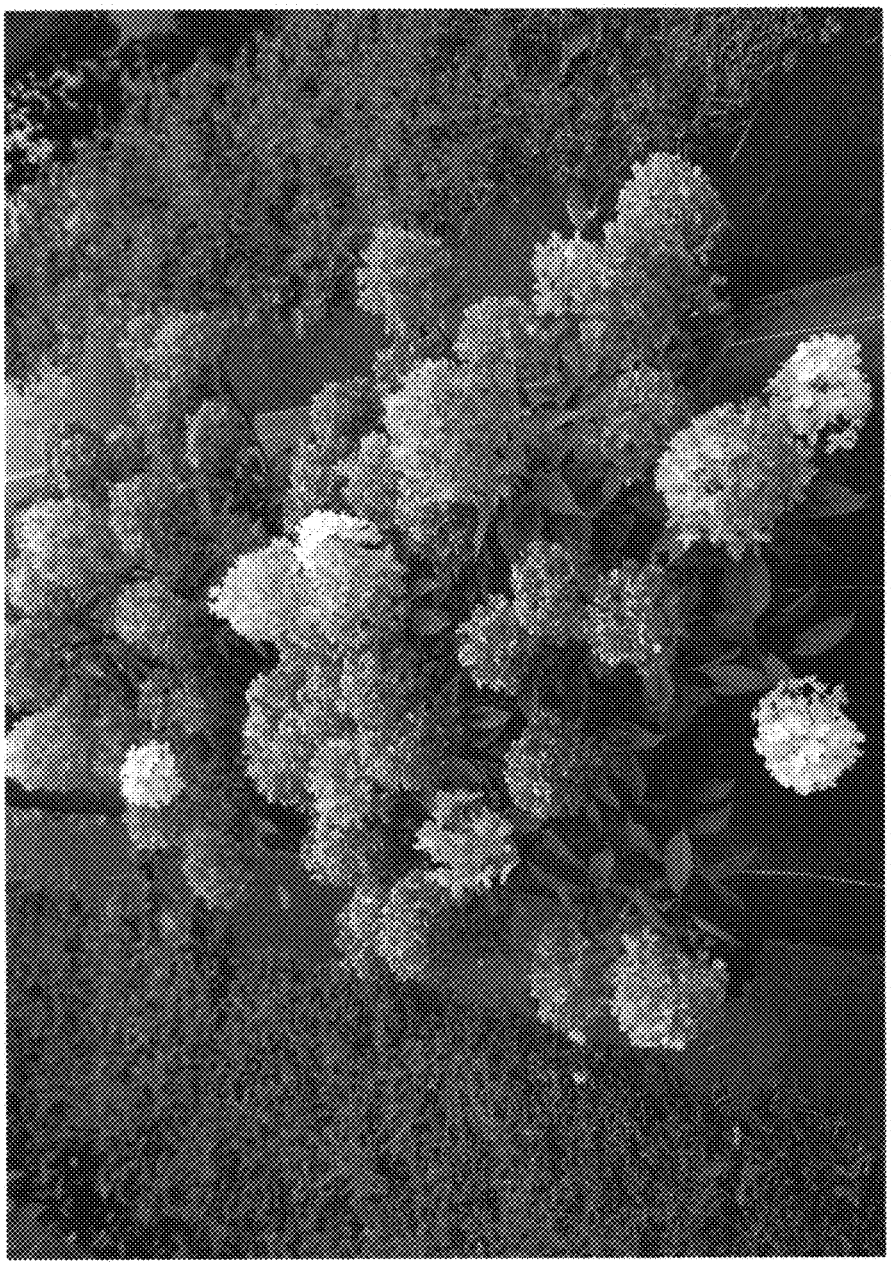
FIG. 2 shows the most mature inflorescence color of a container-grown plant, during late Summer.
Figure 3:
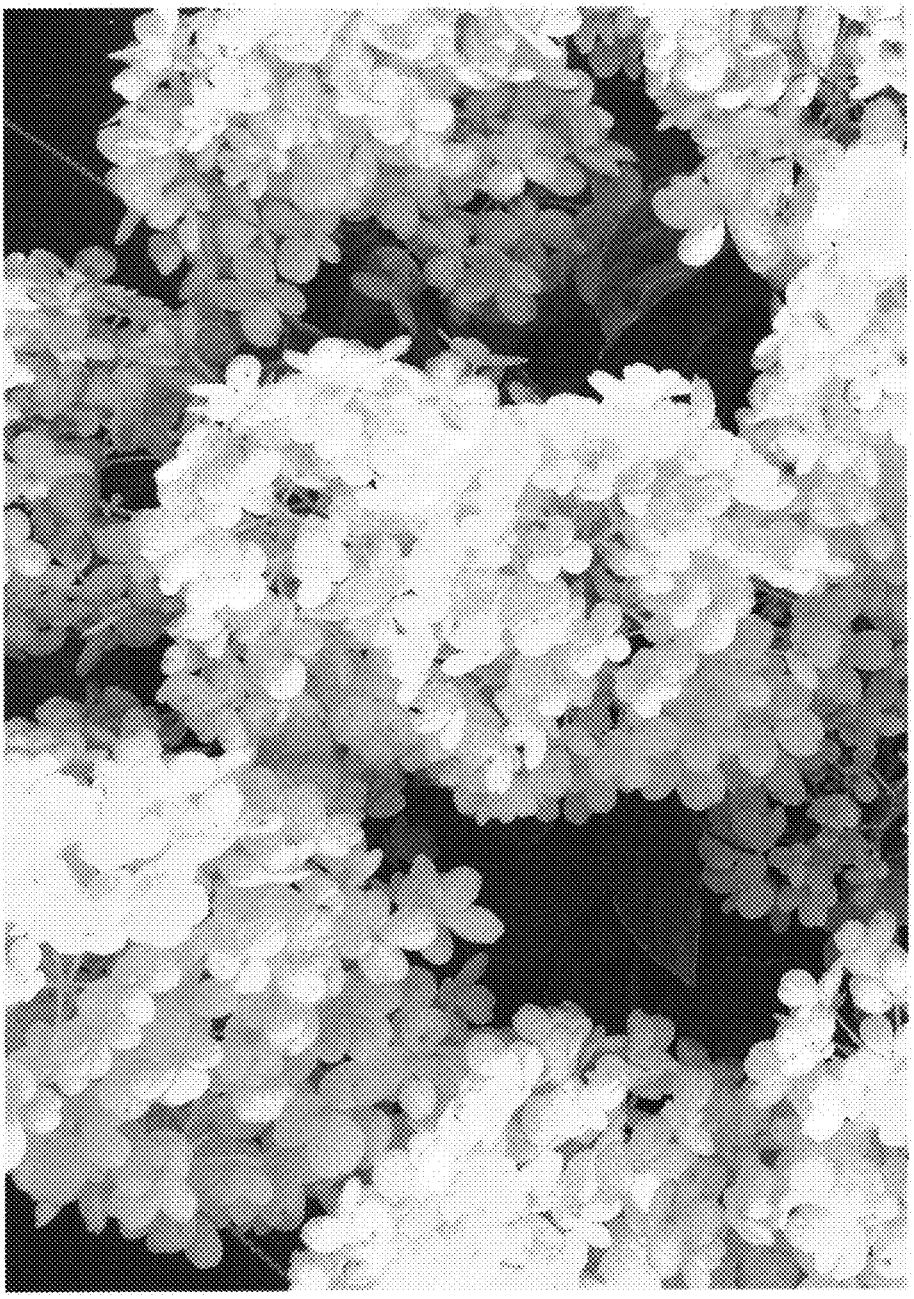
FIG. 3 shows the early Summer color of a mature inflorescence color of a container-grown plant, outdoors in Grand Haven, Mich. in 2019.

In the following description, color references are made to The Royal Horticultural Society Colour Chart 2015 except where general terms of ordinary dictionary significance are used. The following observations and measurements describe 'SMNHPK' plants grown in a commercial poly greenhouse in Grand Haven, Mich. under natural lighting. Measurements were taken during Summer of 2019. The plants were about 4 years old planted in the ground. The growing temperature ranged from 5° C. to 27° C. Measurements and numerical values represent averages of typical plant types.

Botanical classification: *Hydrangea paniculata* 'SMNHPK'.

PROPAGATION

Time to initiate roots: Approximately 18 days.

Time to produce a rooted young plants: Approximately 60 days.

Root description: Fibrous, dense, freely branching, thin to thick roots. White to brown in color, not accurately measured with R.H.S. chart.

Propagation method: Softwood cuttings.

PLANT

Plant type: Flowering deciduous perennial shrub.

Age of plant described: Approximately 2 to 3 years old.

Growth habit: Upward and outward.

Overall plant shape: Upright, rounded, compact.

Height: 34 cm.

Plant spread: 48 cm.

Growth rate: Good.

Plant vigor: Vigorous.

Branching habit: Upright, outward.

Length of primary lateral branches: 20 cm.

Diameter of lateral branches: 5 mm.

Quantity of lateral branches: 10.

Stem:

- *Stem shape*.—Round.
- *Stem strength*.—Strong.
- *Color*.—Immature: RHS Green 143D. Mature: RHS Greyed-Green 197C.
- *Pubescence*.—On new growth.
- *Aspect*.—0 to 45°.

Internode length: 2 to 4 cm.

Root description: Moderately dense, thick main roots with fine, fibrous secondary roots. Main roots colored near Brown 200D, secondary roots near Yellow-White 158D.

FOLIAGE

Leaf:

- *Arrangement*.—Opposite.
- *Leaf shape*.—Elliptic.
- *Average length*.—6 cm.
- *Average width*.—2.75 cm.
- *Apex*.—Acute to attenuate.
- *Base*.—Acute.
- *Margin*.—Serrate.
- *Texture of top surface*.—Slightly course.
- *Texture of bottom surface*.—Smooth, with distinct veins.
- *Leaf pubescence*.—Upper side.
- *Color*.—Young foliage upper side: RHS Yellow-Green 146B. Young foliage under side: RHS Yellow-Green 148B. Mature foliage upper side: RHS Green 139A. Mature foliage under side: RHS Green NN137D.
- *Venation*.—Pattern: Pinnate. Color upper side: RHS Yellow-Green N144D. Color under side: RHS Yellow-Green 145C.
- *Petiole*.—Average Length: 1.5 cm. Diameter: 2 mm. Petiole color upper side: RHS Yellow-Green 144C. Petiole color lower side: RHS Yellow-Green 144C. Petiole Texture upper side: Smooth. Petiole Texture lower side: Smooth.

FLOWER

Natural flowering season: July through August.

Inflorescence:

- *Type*.—Mophead.
- *Quantity of flowers per inflorescence*.—Fertile flowers: 200 to 500. Sterile flowers: 200 to 500.
- *Persistent or self-cleaning*.—Persistent, self-cleaning after several weeks.
- *Longevity*.—Individual flowers stay fresh on the plant for about 2 weeks. Inflorescences are ornamental for several weeks.
- *Fragrance*.—None detected.

Panicle:

- *Shape*.—Panicle.
- *Height*.—14.5 cm.
- *Diameter*.—15 cm.

Sterile flower:

- *Bud shape*.—Globose.
- *Bud length*.—2 mm.
- *Bud diameter*.—2 mm.
- *Bud color*.—RHS White 155A.
- *Flower aspect*.—Outward.
- *Flower length*.—3 mm.
- *Flower diameter*.—3 mm.
- *Flower shape*.—Cruciform.
- *Persistence*.—Persistent.

Sterile flower petals:

- *Petal arrangement*.—Cruciform.
- *Quantity*.—4.
- *Length of petal*.—1.5 mm.
- *Width of petal*.—1 mm.
- *Apex*.—Acute.
- *Shape of petal*.—Lanceolate to oblong.
- *Petal margin*.—Entire.

*Petal base*.—Obtuse.
*Petal texture*.—Smooth, upper and under side.
*Color*.—Upper surface at first opening: RHS White 155A. Under surface at first opening: RHS White 155A. Upper surface at maturity: RHS White 155A. Under surface at maturity: RHS White 155A.

Sterile flower sepal:
*Arrangement*.—Cruciform.
*Number*.—4.
*Shape*.—Obovate.
*Tip*.—Obtuse.
*Base*.—Acute.
*Margin*.—Entire.
*Length*.—1 cm.
*Width*.—8 mm.
*Texture, upper*.—Smooth.
*Texture, lower*.—Smooth.
*Color*.—Upper surface at first opening: RHS White 155A. Under surface at first opening: RHS White 155A. Upper surface at maturity: RHS White 155A. Maturing to have a flush near Red-Purple N57D. Late Summer strongly flushed 61B. Under surface at maturity: RHS White 155A. Maturing to have a flush near Red-Purple 63B. Late Summer strongly flushed 59D. Upper surface, fading: RHS White 155A, covered Red-Purple 59C. Under surface, fading: RHS White 155A, covered Red-Purple 59C.

Sterile flower pedicel:
*Length*.—1.5 cm.
*Diameter*.—1 mm.
*Angle*.—45-90°.
*Strength*.—Moderate.
*Texture*.—Some pubescence.
*Color*.—RHS White 155A.

Fertile flower:
*Shape*.—Rotate.
*Depth*.—4 mm.
*Diameter*.—5 mm.
*Flower aspect*.—Outward.
*Persistence*.—Persistent.
*Longevity*.—1-2 weeks.
*Bud shape*.—Orbicular.
*Bud length*.—2 mm.
*Bud diameter*.—2 mm.
*Bud texture*.—Glabrous.
*Bud color*.—RHS White 155A.

Fertile flower petals:
*Arrangement*.—Whorl.
*Quantity*.—5.
*Length of petal*.—2 mm.
*Width of petal*.—1 mm.
*Apex*.—Acute.
*Shape of petal*.—Lanceolate.
*Petal margin*.—Entire.
*Petal base*.—Truncate.
*Petal texture*.—Smooth, upper and under side.
*Color*.—Upper surface at first opening: RHS White 155A. Under surface at first opening: RHS White 155A. Upper surface at maturity: RHS White 155A. Under surface at maturity: RHS White 155A.

Fertile flower sepal: Inconspicuous.

Fertile flower pedicel:
*Angle*.—90°.
*Strength*.—Moderate.
*Length*.—3 mm.
*Width*.—1 mm.
*Texture*.—Slight pubescence.
*Color*.—RHS White 155A.

REPRODUCTIVE ORGANS

Sterile flowers:
Stamens: Inconspicuous, less than 1 mm.
Anthers: None.
Fertile flowers:
Stamens:
*Number*.—8 to 10.
*Filament length*.—1 mm.
*Filament color*.—RHS White 155A.
Anthers:
*Shape*.—Club.
*Length*.—<1 mm.
*Color*.—RHS White 155A.
*Pollen color*.—RHS White 155A.
*Pollen amount*.—Scant to moderate.
Pistil:
*Number*.—2 lobes.
*Length*.—1 mm.
*Style*.—Length: 0.5 mm. Color: RHS White 155A.
*Stigma*.—Shape: Lobed. Color: RHS White 155A.

OTHER CHARACTERISTICS

Seeds and fruits: None observed.
Disease/pest resistance: Neither resistance nor susceptibility to normal diseases and pests of *Hydrangea* have been observed.
Temperature tolerance: USDA Zones 3 to 9.

What is claimed is:

1. A new and distinct cultivar of *Hydrangea* plant named 'SMNHPK' as herein illustrated and described.

* * * * *